March 28, 1939. W. M. PERRY Plant Pat. 320
PEACH TREE
Filed Aug. 27, 1938
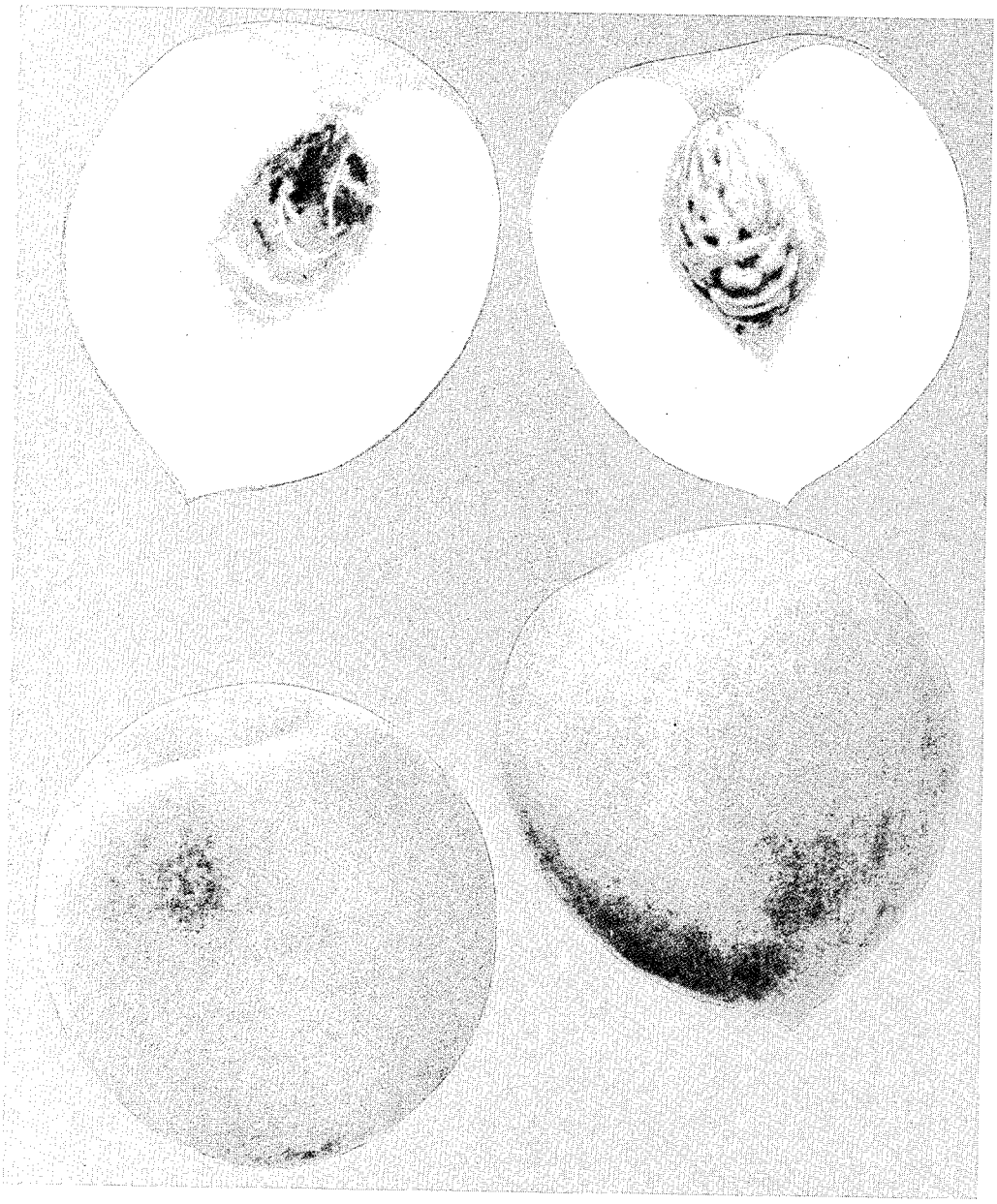
Inventor
W. M. Perry
By Robert Robb
attorneys Patented Mar. 28, 1939

Plant Pat. 320

UNITED STATES PATENT OFFICE

320

PEACH TREE

Willie Marsden Perry, Chase City, Va., assignor to Bountiful Ridge Nurseries, Princess Anne, Md.

Application August 27, 1938, Serial No. 227,206

1 Claim. (Cl. 47—62)

The present discovery relates to a new and distinct variety of peach tree, originating as a chance seedling and found by me to possess important novel characteristics which distinguish it from other known varieties.

The distinguishing characteristics above referred to reside in the color of the fruit, the early period of ripening, and the thickness of the flesh or smallness of the pit in comparison to other varieties.

With reference to the early ripening, this new variety ripens with and slightly after Early Wheeler (Red Bird) and the trees are as vigorous as Red Bird. The trees also set more fruit than the average varieties, the fruit being ordinarily a freestone, though due to excessive rain immediately before the present ripening season it manifests a slight tendency to cling to the stone.

The characteristics above referred to are all important from a commercial standpoint and make the variety very desirable from the marketing viewpoint.

The drawing shows in reduced scale the fruit in side elevation and vertical section.

This new variety has been asexually reproduced and found to come true to form.

The following is a detail description of the new variety, color terms being in accord with Maerz and Paul color chart.

Tree:
- Large; vigorous; spreading; open; round topped; hardy; very productive; regular bearer.

Trunk:
- Stocky; smooth.

Branches:
- Stocky; smooth; brown—gray; glossy.
- *Lenticels.*—Medium.

Leaves:
- Length—14–16 cm.; width—4–4.5 cm.; large; oval; lanceolate; acutely pointed; thick; dark green; smooth.
- *Margin.*—Crenate.
- *Petiole.*—Medium to short; thick.
- *Glands.*—Average, 2–3; opposite; small; reniform; green; position—basal.
- *Stipules.*—Small—do not persist.

Flowers—buds:
- Hardy; size—medium; length—medium; form—conic—plump; appressed—free; pubescent.

Flowers:
- *Dates of first and full bloom.*—March 15 and March 21 (medium compared with other varieties).
- *Size.*—Medium.
- *Color.*—Salmon (Pl. 10–A–7).

Fruit:
- Eating hard—June 18, 1938. Specimens described grown at Chase City, Virginia, U. S. A.
- *Size.*—Uniform—medium—diameter axial 2¼ inches. Transverse in suture plane—2⅜ inches. At right angles to suture plane—2¼.
- *Form.*—Uniform—Symmetrical—oblong—broadly ovoid.
- *Suture.*—A distinct line but discontinuous at apex—has marked depression beyond pistil point.
- *Ventral surface.*—Rounded—slightly lipped toward base; lips—equal.
- *Cavity.*—Flaring—abrupt—elongated in suture plane with suture showing on one side. Depth—⅜ inch. Breadth—½ inch.
- *Base.*—Rounded.
- *Apex.*—Mammiform—rounded. Pistil point—oblique.
- *Stem.*—Length—⅛ inch. Size—medium—glabrous. Adherence to stone—medium.
- *Skin.*—Medium—tough—tenacious to flesh. Tendency to crack—slight, none in wet season. Color—cream Pl. 9–D–4 with red blush. (Carmine 3–K–6). Down—moderate to scant—short.

Flesh:
- Color—white to cream—slightly mottled next to skin or sunny side. Surface of pit cavity—pale—white.
- *Amygdalin.*—Wanting. Juice: abundant—rich to watery.
- *Texture.*—Firm—fine—meaty—melting.
- *Fibres.*—Few.
- *Ripens.*—Even.
- *Flavor.*—Mild—delicate—vinous.
- *Aroma.*—Distinct.
- *Eating quality.*—Good.

Stone:
- Free to semi-free; adheres to flesh slightly over entire surface.
- *Fibres.*—Short; retains short fibres like threads along ridges.
- *Size.*—Small.
- *Length.*—1–1⅛ inches.
- *Breadth.*—⅝–¾ inch.
- *Thickness.*—½ inch.
- *Form.*—Oval.
- *Base.*—Oblique—narrow—oblong. Apex—acuminate.

*Sides.*—Unequal—curved on right. Surface—regular; ridged near base.
*Ridges.*—Rounded.
*Pits.*—Elongated. Ventral edge—thin with wing toward base throughout.
*Dorsal edge.*—Shallow—narrow groove throughout; ridges interrupted.
Use:
Market—dessert.
Keeping quality:
Good.
Resistance to insects:
Good.
*Diseases.*—Good
Shipping quality:
Good.
I claim:

A new and distinct variety of peach tree characterized as to novelty by the early ripening of its fruit, the color and thickness of the flesh of said fruit, the small size of the pit, and the freestone nature of the fruit, substantially as shown and described.

WILLIE MARSDEN PERRY.